United States Patent [19]
Weimer

[11] Patent Number: 5,323,494
[45] Date of Patent: Jun. 28, 1994

[54] BOXING GOGGLES

[76] Inventor: Charles W. Weimer, 1504 N. Lincoln, Fremont, Nebr. 68025

[21] Appl. No.: 69,752

[22] Filed: Jun. 1, 1993

[51] Int. Cl.$^5$ .............................. A42B 3/00; A61F 9/02
[52] U.S. Cl. .......................................... 2/425; 2/428; 2/431; 2/433; 2/452; 116/211; 446/267
[58] Field of Search ............... 2/431, 426, 428, 430, 2/433, 439, 452, 425, 2 R, 206; 446/27, 267; 128/206.24, 206.25, 206.23; 116/211

[56] References Cited

U.S. PATENT DOCUMENTS

| | | | |
|---|---|---|---|
| 924,613 | 6/1909 | Hellawell | 2/426 X |
| 2,729,024 | 1/1956 | Guttmann | 446/267 x |
| 4,556,995 | 12/1985 | Yamamoto | 2/452 X |
| 4,663,785 | 6/1987 | Comparetto | 2/425 X |
| 4,847,921 | 7/1989 | Leutholt et sl. | 2/206 X |
| 4,864,663 | 9/1989 | Horan | 2/206 |

FOREIGN PATENT DOCUMENTS 1031292 3/1953 France .................................. 2/433

Primary Examiner—Peter Nerbun
Attorney, Agent, or Firm—Leon Gilden

[57] ABSTRACT

Boxing goggles include a unitary housing, having a resilient band mounted to side walls of the housing, with through-extending apertures directed through the housing extending from the rear wall through the front wall. The resilient housing structure is arranged to accommodate impact directed to the housing during a boxing procedure.

2 Claims, 4 Drawing Sheets

BOXING GOGGLES

BACKGROUND OF THE INVENTION

1. Field of the Invention

The field of invention relates to sport goggle structure, and more particularly pertains to new and improved boxing goggles providing a resilient housing to accommodate impact.

2. Description of the Prior Art

Boxing goggles of various types are utilized throughout the prior art as indicated by the U.S. Pat. Nos. 4,977,627; 4,556,995; and 3,533,686.

The instant invention attempts to overcome deficiencies of the prior art by providing for a continuous housing of resilient structure arranged to accommodate impact and in this respect, the present invention substantially fulfills this need.

SUMMARY OF THE INVENTION

In view of the foregoing disadvantages inherent in the known types of sport goggle structure now present in the prior art, the present invention provides boxing goggles wherein the same includes a resilient housing having through-extending apertures for accommodating eye openings. As such, the general purpose of the present invention, which will be described subsequently in greater detail, is to provide new and improved boxing goggles which has all the advantages of the prior art sport goggle structure and none of the disadvantages.

To attain this, the present invention provides boxing goggles including a unitary housing, having a resilient hand mounted to side walls of the housing, with through-extending apertures directed through the housing extending from the rear wall through the front wall. The resilient housing structure is arranged to accommodate impact directed to the housing during a boxing procedure.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide new and improved boxing goggles which has all the advantages of the prior art sport goggle structure and none of the disadvantages.

It is another object of the present invention to provide new and improved boxing goggles which may be easily and efficiently manufactured and marketed.

It is a further object of the present invention to provide new and improved boxing goggles which is of a durable and reliable construction.

An even further object of the present invention is to provide new and improved boxing goggles which is susceptible of a low cost of manufacture with regard to both materials and labor, and which accordingly is then susceptible of low prices of sale to the consuming public, thereby making such boxing goggles economically available to the buying public.

Still yet another object of the present invention is to provide new and improved boxing goggles which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
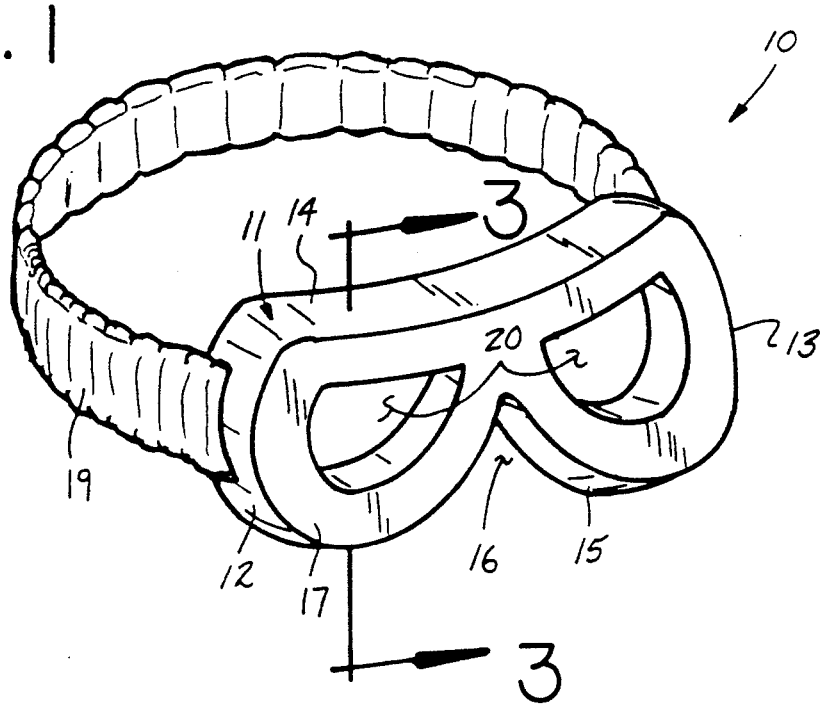
FIG. 1 is an isometric illustration of the invention
Figure 2:
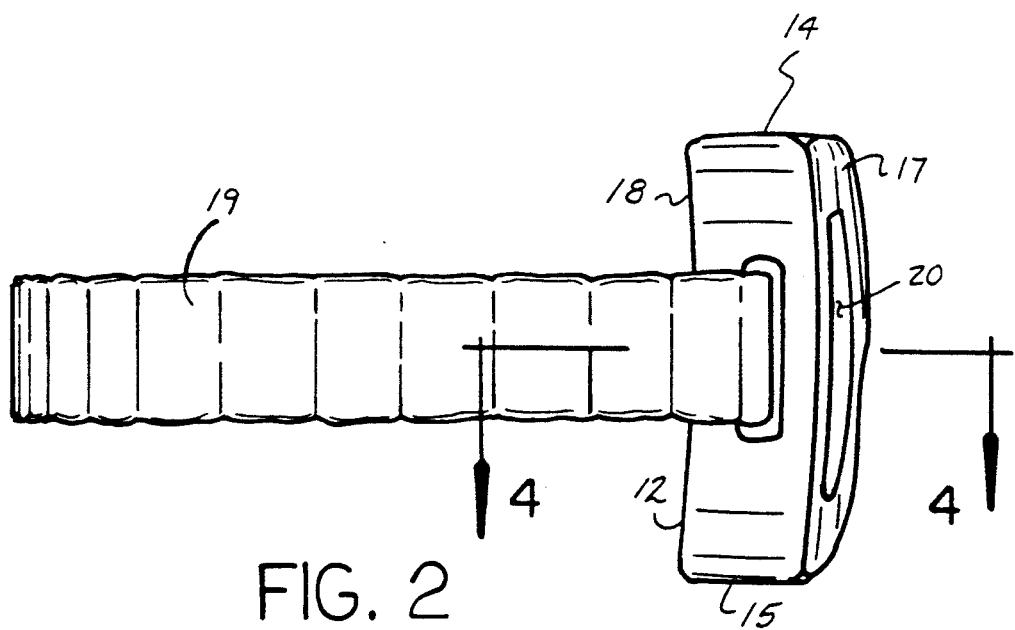
FIG. 2 is an orthographic side view of the invention.
Figure 3:
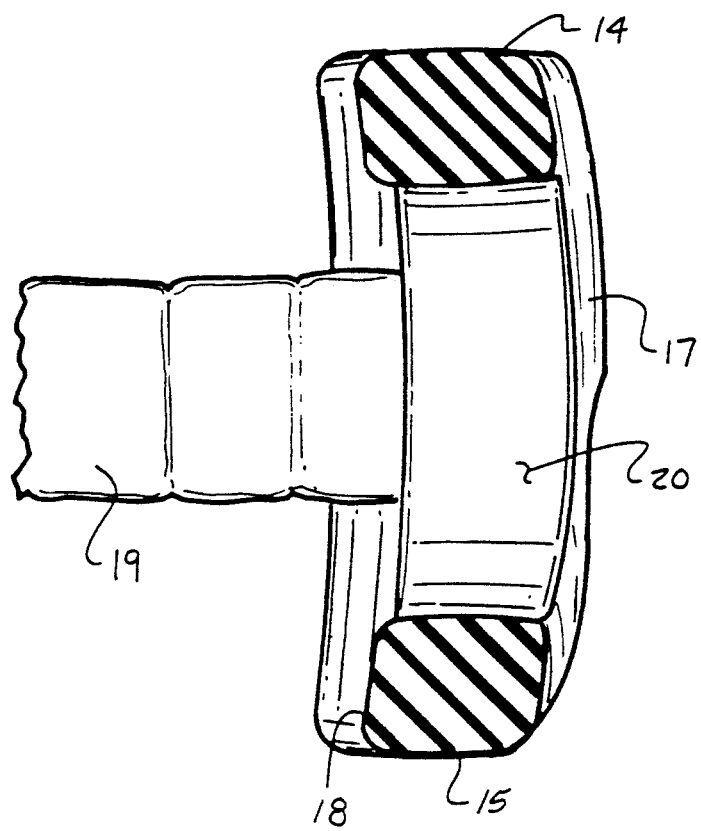
FIG. 3 is an orthographic view, taken along the lines 3—3 of FIG. 1 in the direction indicated by the arrows.
Figure 4:
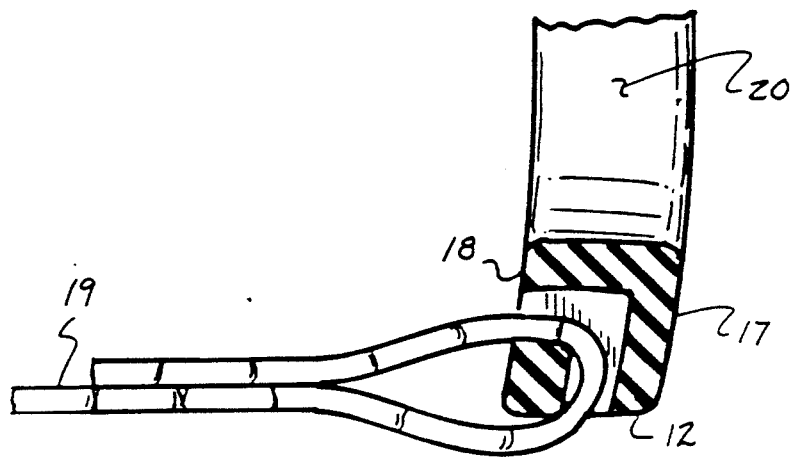
FIG. 4 is an orthographic view, taken along the lines 4—4 of FIG. 2 in the direction indicated by the arrows.

With reference now to the drawings and in particular to FIGS. 1 to 8 thereof, new and improved boxing goggles embodying the principles and concepts of the present invention and generally designated by the reference numeral 10 will be described.

More specifically, the boxing goggles 10 of the instant invention essentially comprises a resilient housing 11, having a first side wall 12 spaced from a second side wall 13, a top wall 14 spaced from a bottom wall 15.

The bottom wall 15 includes a bottom wall recess 16 medially of the bottom wall to accommodate an individual's nose therewithin in supporting the resilient housing 11 upon a centered manner to such an individual. The housing 11 includes a convex iron wall 17 spaced from a concave rear wall 18. A resilient band 19 is mounted to the respective first and second side walls 12 and 13 at opposed first and second ends of the band for securement of the goggle structure about an individual's head positioning the goggles in a secured relationship to an individual during use. Further, spaced eye openings 20 are directed coextensively through the housing from the front wall 17 through the rear wall 18 to accommodate an individual's eyes, with the openings free of obstruction and merely providing protection from impact due to the resilient housing construction.

Figure 5:
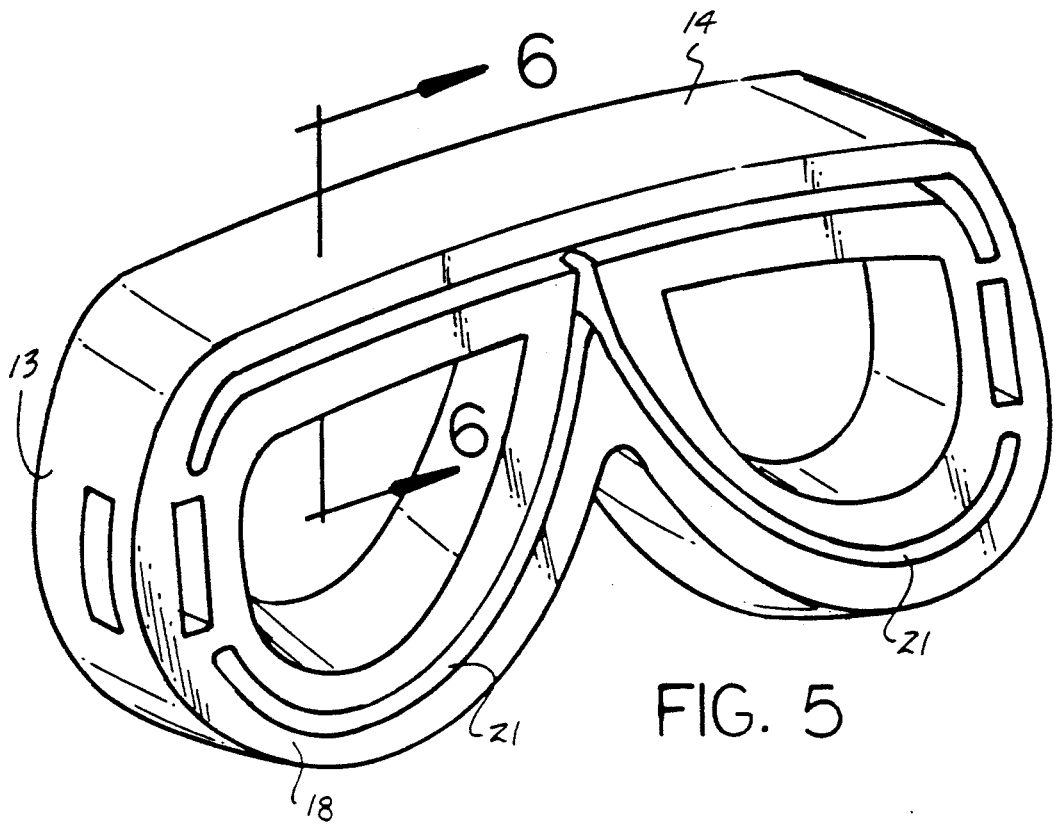
FIG. 5 is an isometric rear view of the invention.
Figure 6:
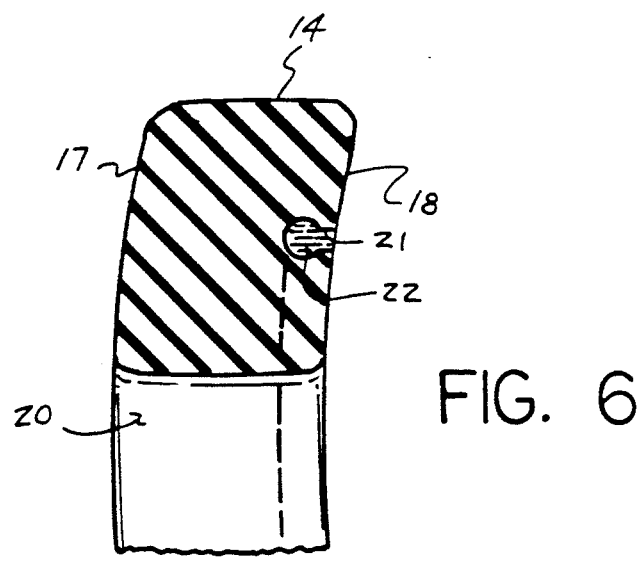
FIG. 6 is an orthographic view, taken along the lines 6—6 of FIG. 5 in the direction indicated by the arrows.

The FIGS. 5 and 6 indicates the use of reservoir grooves 21 mounted in substantially surrounding relationship relative to each of the eye openings 20, having a viscous gel 22 therewithin. Such gel may be in the form of Vasoline (R). The gel in this manner forms a sealing and prevents abrasion of the housing 11 due to the rear wall 18 being directed across an individual's face upon impact.

Figure 7:
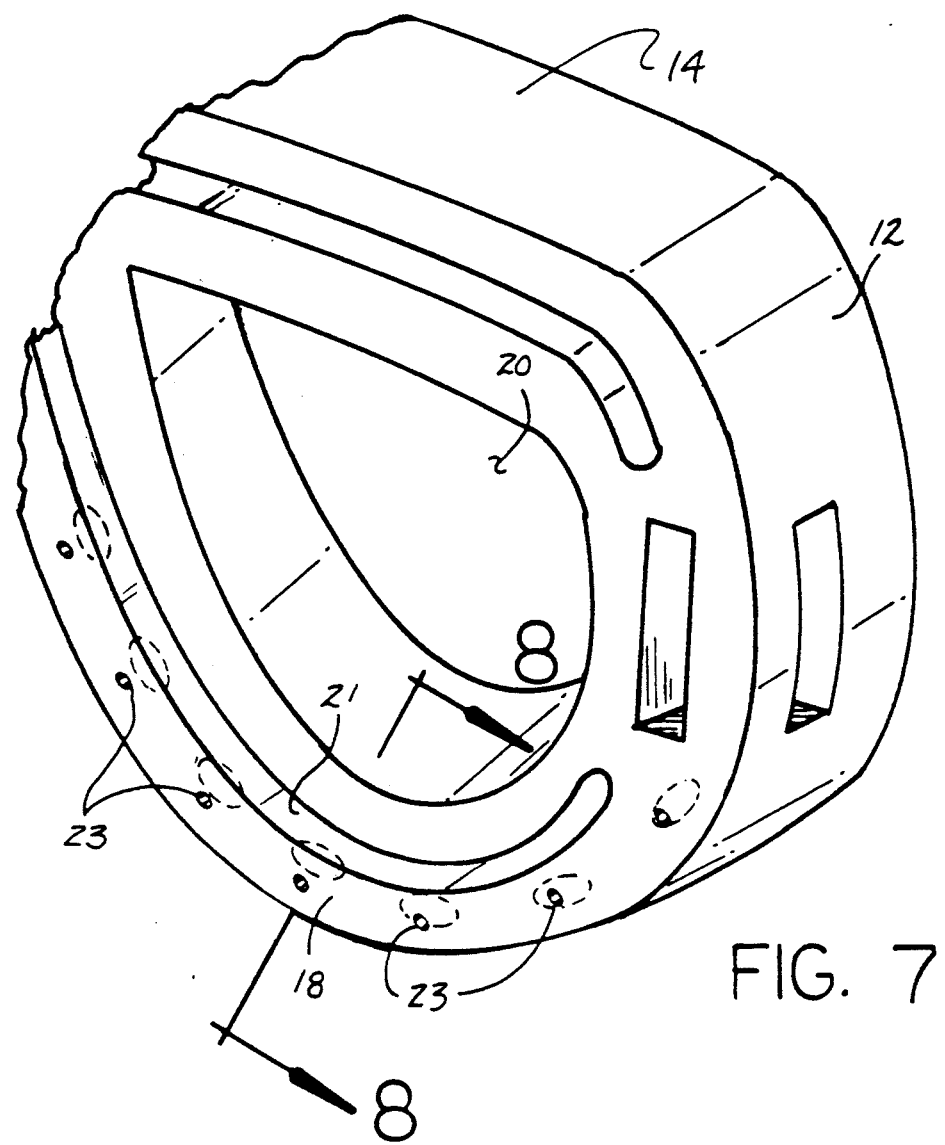
FIG. 7 is an isometric illustration of the rear wall of the goggle structure, including indicator capsules contained therewithin.
Figure 8:
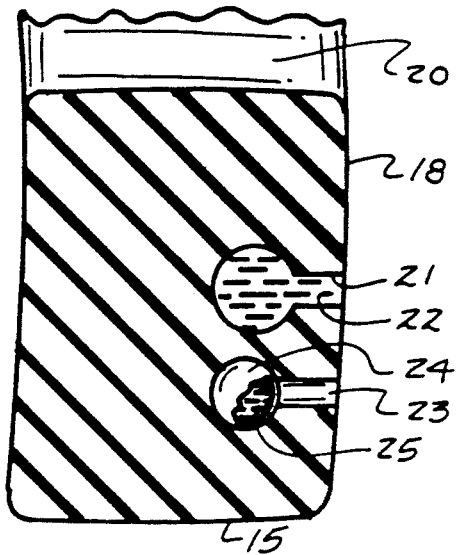
FIG. 8 is an orthographic view, taken along the lines 8—8 of FIG. 7 in the direction indicated by the arrows.

The FIGS. 7 and 8 further includes, in addition to the groove 21, a plurality of bores 23 directed in surrounding relationship relative to each of the eye openings, in a manner as exemplified in FIG. 7, such that each of the bores 23 are directed through the rear wall and are in communication with a frangible capsule 24. The frangible capsule 24 includes a fluid dye 25 therewithin. In this manner, upon rupture of the capsule, the dye is directed through a respective and communicating bore 23 for indicating upon an individual's face where impact has occurred and thusly permit an individual to correct defensive procedures during boxing for use of the goggles as a training device.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. Boxing goggles, comprising,
    a resilient unitary housing, having a first side wall spaced from a second side wall, a top wall spaced from a bottom wall, the bottom wall including a bottom wall recess directed into the bottom wall medially thereof, and
    the housing having a convex front wall coextensive with and spaced from a concave rear wall, and
    a plurality of eye openings positioned at an equal distance from opposed sides of the bottom wall recess, and
    a resilient band, the resilient band having band first and second ends, with the first end mounted to the first side wall, the second end mounted to the second side wall, and
    a plurality of reservoir grooves directed into the rear wall, wherein the reservoir grooves are arranged in surrounding relationship relative to the eye openings, and the grooves include a viscous gel coextensive with the grooves.

2. Boxing goggles as set forth in claim 1 including a plurality of bores directed into the rear wall, and a plurality of frangible capsules positioned within the resilient housing between the front wall and the rear wall, wherein each of the frangible capsules is positioned in communication with one of said bores, each of the frangible capsules includes a fluid dye therewithin permitting rupture of said capsules upon impact directing said fluid dye through a respective one of said bores.

* * * * *